(12) United States Patent
Curtis et al.

(10) Patent No.: US 6,270,890 B1
(45) Date of Patent: Aug. 7, 2001

(54) DENTAL FLOSS

(75) Inventors: John Pierre Curtis, Bloomsbury, NJ (US); Michael Joseph McGreal, Rockville, MD (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 08/059,693

(22) Filed: May 10, 1993

Related U.S. Application Data

(63) Continuation-in-part of application No. 07/729,834, filed on Jul. 11, 1991, now Pat. No. 5,209,251, which is a continuation-in-part of application No. 07/282,962, filed on Dec. 2, 1988, now Pat. No. 5,033,488, which is a continuation-in-part of application No. 07/174,757, filed on Mar. 29, 1988, now abandoned.

(51) Int. Cl.⁷ .................................................. B32B 19/00
(52) U.S. Cl. ............................ 428/357; 428/394; 428/364
(58) Field of Search ..................................... 428/357, 375, 428/379, 394, 364; 132/89, 321; 433/215, 80, 216

(56) References Cited

U.S. PATENT DOCUMENTS

| | | | |
|---|---|---|---|
| 3,664,915 | 5/1972 | Gore | 161/164 |
| 3,699,979 | 10/1972 | Muhler et al. | 132/89 |
| 3,771,536 | 11/1973 | Dragan | 132/89 |
| 3,800,812 | 4/1974 | Jaffe | 132/89 |
| 3,943,949 * | 3/1976 | Ashton et al. | 132/89 |
| 4,033,365 * | 7/1977 | Klepak et al. | 132/89 |
| 4,096,227 | 6/1978 | Gore | 264/210 |
| 4,187,390 | 2/1980 | Gore | 174/102 |
| 4,414,990 * | 11/1983 | Yost | 132/91 |
| 4,776,358 * | 10/1988 | Lorch | 132/321 |
| 4,836,226 | 6/1989 | Wolak | 132/321 |
| 4,935,106 | 6/1990 | Liston et al. | 205/728 |
| 4,996,056 * | 2/1991 | Blass | 132/321 |
| 5,017,339 | 5/1991 | Marsoner et al. | 422/82.04 |
| 5,033,488 | 7/1991 | Curtis et al. | 132/321 |
| 5,209,251 | 5/1993 | Curtis et al. | 132/321 |
| 5,220,932 | 6/1993 | Blass | 132/321 |
| 5,563,042 | 10/1996 | Phillips et al. | 435/14 |
| 5,781,024 | 7/1998 | Blomberg et al. | 324/763 |

FOREIGN PATENT DOCUMENTS

| | | |
|---|---|---|
| WO 94/19683 | 1/1994 | (WO) . |
| WO 94/19684 | 9/1994 | (WO) . |
| WO 97/44672 | 11/1997 | (WO) . |

* cited by examiner

*Primary Examiner*—Merrick Dixon
(74) *Attorney, Agent, or Firm*—Michael J. McGreal

(57) ABSTRACT

The floss is made of a plurality of polytetrafluoroethylene filaments and non-polytetrafluoroethylene filaments. The polytetrafluoroethylene filaments provide for a lubricity for the floss to enter more spaces and the non-polytetrafluoroethylene filaments provide for a case in gripping. In the way a range of polytetrafluoroethylene filaments can be used in the construction of a dental floss.

15 Claims, No Drawings

DENTAL FLOSS

This application is a continuation-in-part of U.S. application Ser. No. 07/729,834 filed Jul. 11, 1991, now U.S. Pat. No. 5,209,251 which is a continuation-in-part of U.S. application Ser. No. 07/282,962 filed Dec. 2, 1988 now U.S. Pat. No. 5,033,488 which in turn is a continuation-in-part of U.S. application Ser. No. 07/174,757 filed Mar. 29, 1988 now abandoned.

BACKGROUND OF THE INVENTION

This invention relates to a multi-filament dental floss where at least a portion of the floss is comprised of polytetrafluoroethylene filaments. More particularly this invention relates to a dental floss where polytetrafluoroethylene filaments comprise from about 10 percent to about 90 percent of the filaments of the dental floss.

Dental flosses come in two different forms. These forms are as multi-filaments and as tapes. As a tape the floss will have a denier of about 1200 to 3000 or more. As multi-filaments the individual filaments have a denier of about 100 to 800. The advantage of a multi-filament over a tape is that in use the filaments of a multi-filament floss splay and assist in the removal of food particles, debris and plaque from between the teeth and under the gum line. This enhanced cleaning comes from the splayed filaments each rubbing the surface of a tooth. The use of a plurality of filaments appears to exhibit an increased removal of certain particles and plaque.

In the present instance the objective is to combine the advantages of polytetrafluoroethylene filaments with those of other filaments. Polytetrafluoroethylene has the advantage of a low coefficient of friction of about 0.08 and lower. Since it has a low coefficient of friction it readily passes through the narrow spaces between teeth. In fact, it is too lubricous and is difficult to grip. This problem of polytetrafluoroethylene being too lubricous can be modified by using the polytetrafluoroethylene filaments in combination with other filaments. These other filaments all have coefficients of friction that are greater than polytetrafluoroethylene. Upon the combination of such filaments with polytetrafluoroethylene the coefficient of friction is increased. The floss has a coefficient of friction that permits it to easily pass between adjacent teeth but yet to be readily gripped. The polytetrafluoroethylene filaments provide lubricity and the non-polytetrafluoroethylene filaments provide for a gripping of the floss.

The state of the art of present commercial dental flosses is exemplified by (U.S. Pat. No. 4,414,990, U.S. Pat. No. 4,033,365 and U.S. Pat. No. 3,943,949 which disclose the use of various non-polytetrafluoroethylene filaments as a floss. U.S. Pat. No. 5,033,488 discloses a different floss the use of a single strand of expanded polytetrafluoroethylene that has been coated with a microcrystalline wax as a floss. The microcrystalline wax increases the coefficient of friction so that the strand of polytetrafluoroethylene can be more easily gripped. The problem of a difficulty in gripping was solved by adding a wax coating. However, this now can also be resolved through the use of a mixture of fibers. The various non-polytetrafluoroethylene fibers that have been used consist of a selection of natural and manufactured filaments. A wax coating is used on nylon and related filaments as a lubricating agent. The most used filament material is nylon. The flosses can be wax coated or have no coating. In addition, the flosses can be coated with a flavorant, fluoride or other substance. The expanded polytetrafluoroethylene that is used is a particular polytetrafluoroethylene.

BRIEF DESCRIPTION OF THE INVENTION

This invention is directed to a dental floss which is comprised of polytetrafluoroethylene filaments and non-polytetrafluoroethylene filaments. The floss can contain from about 10 percent to 90 percent polytetrafluoroethylene filaments and about 90 percent to 10 percent of non-polytetrafluoroethylene filaments. Preferably this is about 30 percent to 70 percent polytetrafluoroethylene filaments and about 70 percent to 30 percent non-polytetrafluoroethylene filaments. The filaments range from about 100 denier to about 800 denier. The polytetrafluoroethylene filaments can be expanded polytetrafluoroethylene but this in most instances will not be the case due to the high cost of expanded polytetrafluoroethylene filaments. The non-polytetrafluoroethylene can be any of a nylon, rayon, dacron, cellulose, cotton, polyester, polyamide, polyethylene, polypropylene, polyacrylate, silicone polycarbonate, styrene butadiene, styrene ethylene-propylenes and thermoplastic polyurethanes. A wide range of fibers can be used. The fibers can be wax coated or non-wax coated. Other similar coatings used in the art also can be utilized. In addition, the filaments can be coated with flavorants and medicaments. Medicaments include fluorides, anti-bacterial agents, cooling agents, coagulants, antibiotics, anti-plaque agents, anti-tartar agents and polishing agents.

The floss as it is formed will undergo a twisting to form the filaments into a more cohesive form. There can be from about 1 to 5 twists per inch of filament.

The floss usually will be dispensed from a spool in the conventional manner.

DETAILED DESCRIPTION OF THE INVENTION

In related application U.S. Ser. No. 07/729,854, filed Jul. 11, 1991 there is disclosed the use solely of a wax coating to increase the coefficient of friction of an expanded polytetrafluoroethylene floss. The content of this application Ser. No. 07/729,854 is incorporated herein by reference. In this present application there is set forth an additional technique for increasing the coefficient of friction of a floss that contains polytetrafluoroethylene filaments.

The present floss is one that is a mixture of polytetrafluoroethylene filaments and non-polytetrafluoroethylene filaments. The polytetrafluoroethylene filaments provide lubricity and the non-polytetrafluoroethylene filaments provide the ability to grip the fibers. Further, since the floss is comprised of a plurality of filaments they will splay against tooth surfaces during usage and provide for a good cleaning of the teeth.

The filaments should be of a denier of about 100 denier to 800 denier. The floss will then be comprised of from about 2 to 20 filaments. The filaments will be present in a random mixture and will be twisted with about 1 to 5 twists per inch to provide integrity to the floss, but yet permit the floss to splay when it contacts tooth surfaces. The floss can also have a wax coating. A useful coating is a microcrystalline wax coating. However, essentially any naturally occurring or synthetic wax can be used as long as the melting point of the wax is above at about 45° C. and the wax is not brittle at about 25° C. Other suitable waxes are beeswax, paraffin wax and carnauba wax.

The floss can also be coated with a flavorant and/or medicant. A preferred form of flavorant is a spray dried flavorant. The flavorant can be essentially any flavor but is preferably a peppermint and/or spearmint. This can be applied to the filaments using a non-wax polymeric binder as is described in U.S. Pat. No. 4,033,365. If the floss is wax coated the spray dried flavorant can be applied to the still molten wax.

The medicaments that can be applied to the floss include anti-bacterial agents such as triclosan, chlorhexidine, iodine, sulfonamides, bisbiguanides and phenols, coagulants such as K vitamins (1–4), calcium ions in the form of a water soluble calcium salt and blood factors, fluorides such as sodium fluoride, sodium monofluorophosphates and stannous fluoride, a ntibiotics such as tetracyclines, neomycin, or mehonidazole, anti-inflammatory such as aspirin, maproxen, ibuprofen, flurbiprofin, eugenol or hydrocortisone, anticalculus agents such as the soluble pyrophate salts, desentisizing agents such as strontium chloride or sodium fluoride, local anesthetic agents such as lidocaine or benzocaine, peroxides such as urea peroxide, coolants astringents and polishing agents. The medicaments can be applied to the floss filaments as a liquid and dried onto the filaments or they can be applied to the filaments as a solid with the aid of a binder. Flavorants can be applied as spray dried solids. A suitable binder is polyvinyl alcohol, and in particular, in combination with polyethylene glycol.

The polytetrafluoroethylene filaments can be a polytetrafluoroethylene without subsequent processing or an expanded polytetrafluoroethylene as is described in U.S. Pat. No. 5,033,488. An expanded polytetrafluoroethylene is a polytetrafluoroethylene that has been rapidly stretched, preferably at an elevated temperature. Regardless of whether the polytetrafluoroethylene filament is a virgin, stretched or expanded polytetrafluoroethylene, it will have a coefficient of friction of less than about 0.08. The useful non-polytetrafluoroethylene filaments include nylon, rayon, dacron, cellulose, cotton, polyester, polyamides, polypropylene, polyacrylates, silicone polycarbonate, styrene butadienes, styrene ethylene propylenes and thermoplastic polyurethenes. The useful filaments will have a coefficient of friction of at least about 0.1 and preferably about 0.2.

The polytetrafluoroethylene filaments will comprise from about 10 percent to 90 percent of the filaments of the floss with the remainder being non-polytetrafluoroethylene filaments. In most instances the polytetrafluoroethylene filaments will comprise 30 percent to 70 percent of the filaments of the floss with the remainder being non-polytetrafluoroethylene filaments.

In providing the floss, the composition of the filaments is chosen. The number of filaments will be from 2 to 20 and preferably about 2 to 10 depending on the denier of the filaments. The filaments are twisted with about 1 to 5 twists per inch to form the ribbon of floss. The twisting provides integrity of the floss on the spool and during subsequent handling. However, when used the filaments will spread out and splay against tooth surfaces. The filaments of the floss can be coated with a wax before or after twisting, preferably after twisting, where the floss is to be a wax coated floss. Other additives will be applied to a wax coated floss after the wax coating. The flavor can be applied as a liquid or a solid. It is preferred to use a spray dried solid. Likewise, the various other additives can be applied as a liquid or a solid. When applied as a liquid the floss is dried prior to being wound onto a spool. The drying can be by radiant drying or air drying. After drying, the floss is wound onto a spool.

In use approximately an eighteen inch length of floss is cut from the spool and used to clean the surfaces of the teeth, and in particular, the side surfaces and the subgingival surfaces. The present floss splays on contact with the teeth.

EXAMPLE

This example provides a comparison of the coefficients of friction of a selection of dental flosses.

The coefficient of friction is determined by the force required to move an object across a surface. The coefficient of friction is determined using an Instron 1100 instrument where the floss is moved across two mandrels having a defined surface by the drawing force of a 100 gram weight. The coefficient of friction is calculated by the following formula:

$$COF = (1/\text{rad})\ln(T_2/T_1)$$

The results of the coefficient of friction tests for a sampling of flosses is as follows:

| Floss | Denier | Coefficient of Friction |
|---|---|---|
| Polytetrafluoroethylene (1 end) | 500 | |
| Nylon Blend (3 ends) | 140 | 0.205 |
| Polytetrafluoroethylene (1 end) | 500 | |
| Nylon (3 ends) | 140 | 0.210 |
| Expanded Polytetrafluoroethylene (Wax Coated) (1 end) | 1200 | 0.200 |
| Polytetrafluoroethylene (1 end) | 500 | |
| Nylon (1 end) | 140 | 0.293 |
| Polytetrafluoroethylene (1 end) | 250 | |
| Nylon (1 end) | 140 | 0.236 |
| Polytetrafluoroethylene (1 end) | 290 | |
| Nylon (1 end) | 140 | 0.258 |

(An end is a filament)

What is claimed is:

1. A dental floss comprised of a plurality of filaments which are a mixture of polytetrafluoroethylene and non-polytetrafluoroethylene filaments, said filaments being twisted together with about 1 to 5 twists per inch.

2. A dental floss as in claim 1 wherein said polytetrafluoroethylene filaments comprise from about 10 percent to 90 percent of the filaments of said floss.

3. A dental floss as in claim 2 wherein said polytetrafluoroethylene filaments comprise from about 30 percent to 70 percent of the filaments of said floss.

4. A dental floss as in claim 1 wherein said filaments are of a denier of about 100 to 900.

5. A dental floss as in claim 2 wherein said filaments are of a denier of about 100 to 800.

6. A dental floss as in claim 1 wherein said non-polytetrafluoroethylene filament is selected from the groups consisting of nylon, rayon, dacron, cellulose, cotton, polyester, polyamides, polypropylene, polyacrylates, silicone polycarbonates, styrene butadienes, styrene ethylene propylenes and thermoplastic polyurethenes.

7. A dental floss as in claim 2 wherein said non-polytetrafluoroethylene filament is selected from the group consisting of nylon, rayon, dacron, cellulose, cotton, polyester, polyamides, polypropylene, silicone polycarbonates, styrene butadienes, styrene ethylene propylenes, polyacrylates and thermoplastic polyurethenes.

8. A dental floss comprised of plurality of filaments which are a mixture of nylon filaments and polytetrafluoroethylene filaments, said filaments being twisted together with about 1 to 5 twists per inch.

9. A dental floss as in claim 8 wherein said polytetrafluoroethylene filaments comprise from about 10 percent to 90 percent of the filaments of said floss.

10. A dental floss as in claim 9 wherein said polytetrafluoroethylene filaments comprise from about 30 percent to 70 percent of the filaments of said floss.

11. A dental floss as in claim 8 wherein said filaments are of a denier of about 100 to 800.

12. A dental floss comprised of a plurality of filaments which are a mixture of polyester filaments and polytetrafluoroethylene filaments, said filaments being twisted together with about 1 to 5 twists per inch.

13. A dental floss as in claim 12 wherein said polytetrafluoroethylene filaments comprise from about 10 percent to 90 percent of said filaments.

14. A dental floss as in claim 13 wherein said polytetrafluoroethylene filaments comprise from about 30 percent to 70 percent of said filaments.

15. A dental floss as in claim 12 wherein said filaments are of a denier of about 100 to 800.

\* \* \* \* \*